United States Patent [19]

Apstein

[11] 4,314,550
[45] Feb. 9, 1982

[54] METHOD OF TREATING AN ARRESTED HEART

[75] Inventor: Carl S. Apstein, Waban, Mass.

[73] Assignee: The Trustees of Boston University, Boston, Mass.

[21] Appl. No.: 145,544

[22] Filed: May 1, 1980

[51] Int. Cl.$^3$ .................. A61B 17/00; A61B 19/00
[52] U.S. Cl. .................................. 128/1 D; 128/64; 128/DIG. 3
[58] Field of Search .......... 128/1 R, 1 D, 64, DIG. 3; 435/283

[56] References Cited

U.S. PATENT DOCUMENTS

| | | | |
|---|---|---|---|
| 3,478,737 | 11/1969 | Rassman | 128/64 |
| 3,496,932 | 2/1970 | Prisk et al. | 128/64 |
| 3,769,960 | 11/1973 | Robinson | 128/1 D |
| 3,892,628 | 7/1975 | Thorne et al. | 435/283 |
| 3,914,954 | 10/1975 | Doerig | 435/283 |
| 3,995,444 | 12/1976 | Clark et al. | 128/DIG. 3 |
| 4,048,990 | 9/1977 | Goetz | 128/64 |

OTHER PUBLICATIONS

Apstein, Carl S. et al, "Graded Global Ischemia & Reperfusion", *Circulation*, vol. 55, No. 6, pp. 863–872, Jun. 1977.
"Resuscitation and Circulatory Support by Mechanical Cardiac Massage in Man" Base et al, Biomedical Sciences Instrumentation, vol. 5, 5-23-68.
Apstein, Carl S. et al., "Ventricular Contracture and Compliance Changes with Global Ischemia and Reperfusion and Their Effect on Coronary Resistance in the Rat", *Circulation Research*, vol. 41, No. 2, Aug. 1977, pp. 206–217.
Apstein, Carl S. et al, "Acute Cardiac Ischemia and Reperfusion; Contractility, Relaxation, and Glycolysis", *Am. J. Physiol.*, 235(6), pp. H637–H648, ©1978.
Apstein, Carl S. et al, "Limitations of Laetate Production as an Index of Myocardial Ischemia", *Circulation*, vol. 60, No. 4, Oct. 1979, pp. 877–888.
Ogilby, J. David et al, "Effects of Retrograde Systolic Stretch of Ischemic Myocardium", *Am. J. Cardiology*, vol. 43, May, 1979.
Briggs, Lance et al, "Preservation of Myocardial Compliance During Ischemic Arrest by Applied Intermittent Ventricular Stretch", *Am. J. Cardiology*, vol. 45, Feb. 1980.

*Primary Examiner*—Paul J. Hirsch
*Attorney, Agent, or Firm*—Hamilton, Brook, Smith & Reynolds

[57] ABSTRACT

A heart in induced arrest such as ischemic arrest during a surgical operation is treated to protect it from stiffness, rigor, contracture and a decrease in diastolic compliance or elasticity by periodically stretching the ventricular muscle throughout the period of arrest. The ventricular muscle is stretched by positioning a balloon within the ventricle and expanding that balloon by an incompressible fluid. Preferably, the ventricular volume is expanded such that the resultant pressure on the ventricle wall early in the period of arrest is about equal to the peak systolic pressure prior to arrest. A pressure transducer is associated with the balloon to provide an indication of diastolic properties of the ventricular muscle prior to and after stretching of the muscle.

25 Claims, 6 Drawing Figures

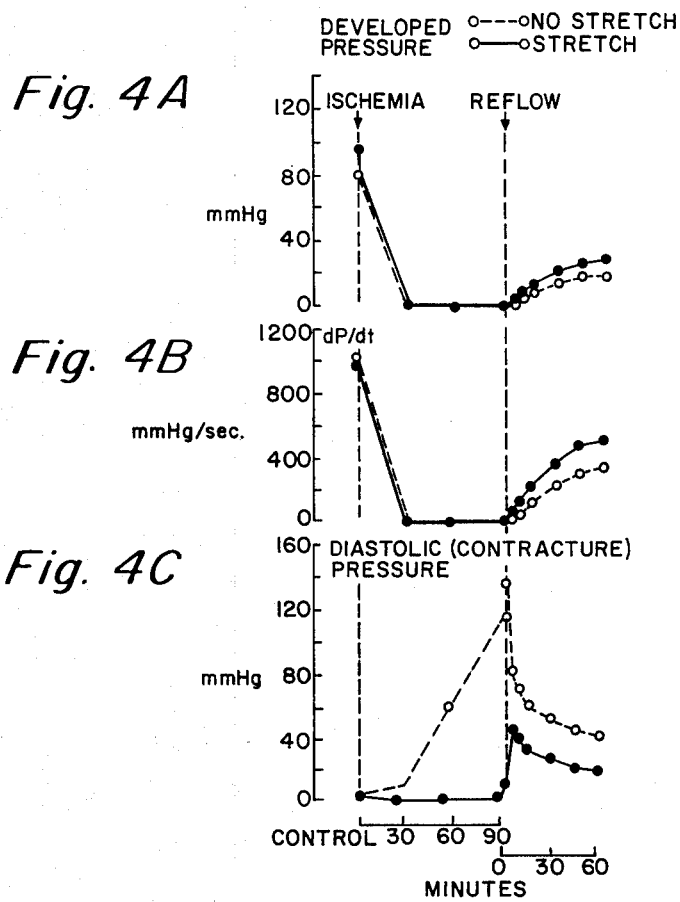

METHOD OF TREATING AN ARRESTED HEART

GOVERNMENT SUPPORT

Work relating to this invention was partially supported by grants from the National Institute of Health: 1-KO4-HL00425 and RO1-HL23406.

TECHNICAL FIELD

This invention relates to the treatment of an arrested heart and has particular application to the protection of a heart from the stiffness, rigor, contracture and decrease in diastolic compliance which occur during the ischemic arrest, cardioplegic arrest, or arrest of the heart by other mechanisms during a surgical operation.

BACKGROUND

The human heart is a muscular organ that functions as two parallel two-stage pumps. Blood is delivered to the left and right ventricles by left and right auricles when the ventricular muscles are relaxed. Then, the ventricular muscles contract and forcefully pump the blood through arteries. If the ventricular muscles are not adequately relaxed or are in a state of rigor during diastole, that is when blood flows into the ventricles, the ventricular filling volume is reduced and the amount of blood which can be pumped from the heart with each beat is reduced. Further, any rigidity of the ventricular muscle, whether due to contracture of the muscle or a passive inelasticity, also reduces the amount of blood which can be pumped into the ventricle during the diastolic state. Once the ventricle is filled to a diastolic volume, as limited by any diastolic rigor, contracture, passive elasticity or diastolic compliance, the contraction of the ventricular muscle pumps that volume of blood into the arteries. The strength of that pumping action is another indication of the condition of the heart.

During heart surgery the heart is bypassed by a mechanical blood pump, and the heart is arrested to enable the surgeon to operate. The ventricular chamber is evacuated and, conventionally, the supply of blood to the coronary arteries to oxygenate the heart muscles is cut off, resulting in global ischemia.

Prolonged myocardial arrest, particularly in combination with ischemia or hypoxia, results in myocardial rigor or contracture. During the ischemic arrest of cardiac surgery this process is recognized in its most extreme form as the "stone heart" syndrome. Mild degrees of contracture which do not cause the fullblown stone heart syndrome can significantly decrease diastolic ventricular compliance, impede diastolic ventricular filling and reduce cardiac output. Two recent clinical reports indicate that such a decrease in left ventricular diastolic compliance commonly occurs in patients undergoing open heart surgery, especially when the period of ischemic arrest lasts longer than 40 minutes. Spotnitz et al., "Effects of open heart surgery on end-diastolic pressure—diameter relations of the human left ventricle," Circulation 59: 662–671, 1979, and Chitwood et al., "Effects of global ischemic arrest on ventricular compliance in man as determined by pulse transit sonomicrometry," Am J Cardiol 43: 378, 1979. Ischemic contracture appears to result from the formation of rigor bonds between actin and myosin. These bonds form when the intracellular adenosine triphosphate concentration falls below a critical level, and the contracture process itself further accelerates the hydrolysis of adenosine triphosphate.

An object of the invention is to provide means for protecting an arrested heart against the deleterious effects of a sustained arrest and, particularly, of an ischemic arrest.

DISCLOSURE OF THE INVENTION

In accordance with this invention, a heart is protected against the deleterious effects of sustained arrest by expanding the ventricular volume a significant amount during the period of arrest to stretch the wall of the heart and its muscle fibres. Experiments have indicated that this results in reduced diastolic contracture during and after the arrest as well as increased heart strength subsequent to the arrest.

In the preferred form of the invention, the ventricular volume is expanded by filling the ventricle with a fluid. Preferably, the fluid is contained in a balloon which is placed within the ventricle and a fluid pressure transducer is associated with that balloon. The balloon may be expanded to a first control volume which is slightly greater than the diastolic volume of the ventricle without contracture to measure the subsequent diastolic contracture of the heart muscle. The volume is also raised to a substantially greater stretch volume to stretch the ventricular muscle during the arrest to reduce contracture of the muscle. Preferably, the stretching of the muscle is over short, widely spaced intervals which do not substantially interfere with the surgeon's work. The stretching may be made in response to the measured diastolic pressure on the balloon.

Preferably, the stretching volume is such that the pressure on the ventricular walls early in the arrest period is about equal to the peak systolic pressure prior to arrest.

BRIEF DESCRIPTION OF THE DRAWINGS

FIG. 4 illustrates the developed pressure of the ventricle, and the rate of change of that pressure, and the diastolic pressure of the ventricle in hearts with and without stretching during and after ischemic arrest.

PREFERRED MODE OF CARRYING OUT THE INVENTION

Figure 1:
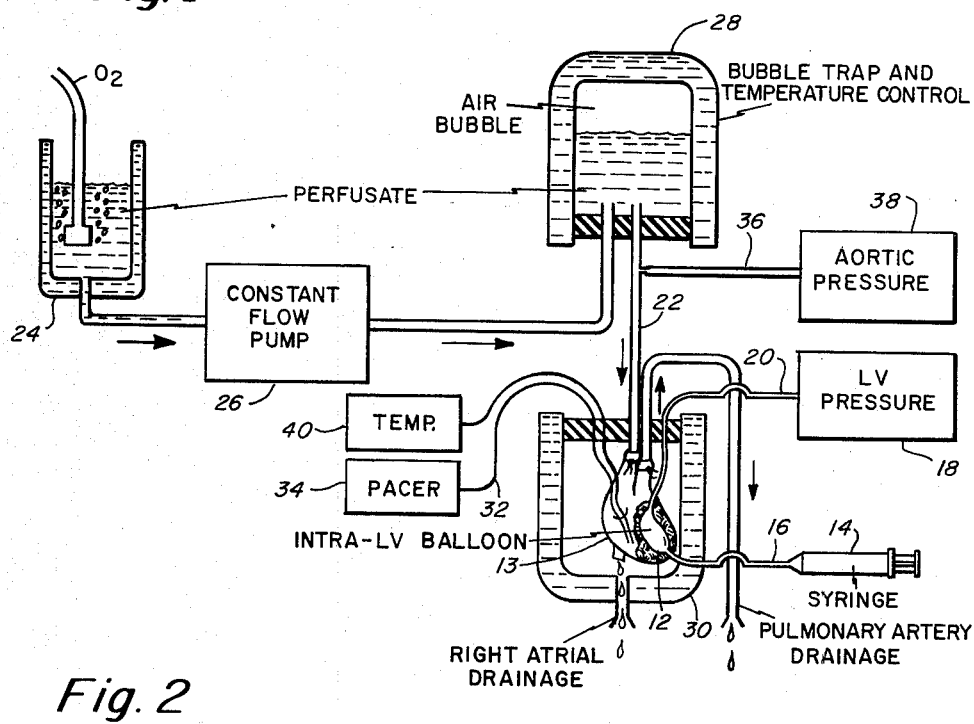
FIG. 1 is a schematic of the test apparatus for stretching the ventricular wall of an arrested heart, for providing flow of a blood substitute through the coronary blood vessels before and after ischemia, and for monitoring the ventricular pressure.

As noted above, ischemic contracture appears to result from the formation of rigor bonds between actin and myosin. I hypothesize that a mechanical stretch, intermittently or continuously applied to the ventricular wall during ischemic arrest, disrupts rigor or contracture bonds which form or prevents their formation and can thereby restore a more normal diastolic compliance to the ventricle. To provide that stretching action, a balloon 12 is placed in the ventricle of a heart and the balloon is inflated with an incompressible fluid by means of a syringe 14 through a cannula 16. The pressure of the fluid within the balloon is monitored by pressure transducer 18 through another cannula 20.

During a surgical operation in which the heart is arrested, the balloon 12 is inflated to the extent necessary to reduce diastolic contracture of the heart. If the balloon is expanded periodically, the periods between expansion or collapse should be as long as feasible so that the work of the surgeon will not be unduly interrupted.

In order to provide stretching action to the muscle only when there is an indication that such stretching is required, the balloon 12 may be inflated to a monitoring volume which is just greater than the diastolic volume of the ventricle during the early portion of the arrest. With a constant volume of incompressible fluid in the balloon, diastolic properties of the ventricular muscle, such as contracture and stiffness, during the arrest are indicated by an increase in pressure in the fluid as detected by the pressure transducer 18. When that pressure exceeds some predetermined threshold, the balloon can be futher expanded to a stretching volume for a short interval and then returned to the pressure monitoring volume, thereby varying the lengths of the heart muscle fibers. The contracture of the muscle can thereby be substantially reduced.

Alternatively, the balloon can be left deflated for predetermined intervals of time and then be inflated to the stretching volume to provide the needed stretching of the ventricular muscle at the end of each interval. The intervals between stretching can be selected to provide for a substantially reduced diastolic contracture after the arrest without unduly interrupting the surgical operation.

As a further alternative, the balloon may be left expanded for a prolonged period of time to apply stretch to the ventricular wall fibers and prevent or reduce the contracture or stiffening process.

The apparatus of FIG. 1 was used to demonstrate the beneficial effects of stretching the ventricular muscle during an ischemic arrest. In the experiment, isolated rabbit hearts, such as at 13, containing a fluid-filled left ventricular balloon 12 were subjected to 90 minutes of normothermic total global ischemia followed by 60 minutes of reperfusion with a blood substitute. In one group (no-stretch group) the left ventricular balloon remained collapsed throughout most of the ischemic period. It was filled to a control, pre-ischemic diastolic volume every thirty minutes to measure the degree of contracture. In a second group (stretch group) every five minutes during the period of ischemia the balloon was expanded to a volume approximately twice as large as the control diastolic volume to stretch the wall of the ventricle.

The experiment was carried out as follows. Albino New Zealand male rabbits weighing 1-2 kg were decapitated and the thorax quickly opened. The heart was rapidly cooled with chilled saline making it asystolic during the operative period. The aorta was dissected free, an incision was made at the level of the right innominate artery, and a cannula 22 was tied into the root of the aorta. Retrograde coronary perfusion of an oxygenated blood substitute was immediately started from a constant pressure perfusion reservoir (not shown) at a pressure head of 75 mm Hg. In this way coronary perfusion was maintained while the heart was being removed from the animal and only a few seconds elapsed between the time of decapitation and the onset of experimental coronary perfusion.

As soon as the coronary arteries were perfused from the constant pressure reservoir, the left ventricle was decompressed by an apical puncture. A drain was placed in the apex of the left ventricle so that it remained free of intra-left ventricular fluid from Thebesian drainage. The heart was then dissected, removed from the thorax, and placed in a water-jacketed, constant temperature chamber 30 which kept the heart at $35° \pm 0.5°$ C. during the preischemic control and postischemic reflow periods; during the period of total ischemia intracardiac temperature decreased by $2°$ C. After placement of the heart in the chamber, coronary perfusion was switched from the fixed pressure reservoir to the system of FIG. 1. That system includes a constant flow pump 26 for pumping an oxygenated blood substitute from a water-jacketed reservoir 24 through a water-jacketed bubble trap and temperature controller 28.

A double-cannulated latex balloon 12 was inserted into the left ventricle; one cannula 16 exited via the site of an apical ventricular puncture and the other cannula 20 exited via the mitral valve orifice. The cannulas were tied in place and the upper (mitral valve) cannula was connected to a pressure transducer 18 to monitor intraventricular pressure. The apical cannula was connected to a hand-held syringe 14 which was intermittently used to expand the intraventricular balloon and stretch the myocardium in the experimental group.

A right ventricular pacemaker wire 32 was inserted via a right atrial incision and attached to a pacer 34. The heart was stimulated by the pacer 34 at a rate of 180/min during the preischemic control and postischemic reflow periods. A 5 V. unipolar stimulus of 5 msec duration was used. The rate of 180/min consistently exceeded endogenous pacemaker rates and thus permitted comparison of contractile function in the two groups, during the pre-ischemic and post-ischemic phases of experiments, at a constant and identical heart rate.

The coronary venous drainage, comprising all of the flow through the right side of the heart, emerged via the pulmonary artery and cut vena cavae, and was collected and pooled for metabolic measurements. The perfusate efflux from the heart was not recirculated. The perfusate from the reservoir 24 consisted of modified Krebs-Henseleit buffer: 118 mM NaCl, 4.7 mM KCl, 2.0 mM $CaCl_2$, 1.2 mM $KH_2PO_4$, 1.2 mM $MgSO_4$, 25 mM $NaHCO_3$, 0.4 mM $Na_2$ EDTA, 5.5 mM glucose, and 1.0 mM lactate. Lactic acid was neutralized with NaOH before being added to the buffer; lactate was added to the perfusate so that aerobic myocardial lactate extraction could be measured. The perfusate was gassed with 95% $O_2$, 5% $CO_2$.

Left ventricular pressure, dP/dt and aortic (coronary perfusion) pressure were monitored continuously throughout each experiment and recorded periodically. Left ventricular pressure was recorded via a 30 cm length of polyethylene tubing 20 (I.D.=0.045 inch) which connected the intraventricular balloon 12 to a Statham P23Db transducer 18. Aortic root pressure was measured through tubes 22 and 36 by transducer 38. Left ventricular dP/dt was obtained from transducer 18 via a DC differentiator circuit. Heart temperature was monitored by a temperature device 40.

To measure the ventricular pressure the relationship between balloon size and left ventricular size is an important consideration. The balloon was slightly larger than the ventricular cavity so that, as the balloon was filled to about the diastolic volume, a rise in the recorded intraballoon pressure was due to increasing ventricular wall tension rather than balloon wall tension. The pressure-volume filling curve of the isolated balloon was measured before and after each experiment; the experiments were always performed on the flat portion of the balloon's pressure-volume curve.

During a 30 min. pre-ischemic control period, coronary flow from pump 26 was 30 ml/min (approximately 10 ml/min/gm of left ventricle). The collapsed intraventricular balloon 12 was slowly filled with fluid while left ventricular pressures were recorded; during the initial 15 min. of the control period the balloon volume was adjusted to give a peak left ventricular systolic pressure of 60-90 mm Hg with a diastolic pressure of less than 10 mm Hg. This level of isovolumic contractile function allowed us to monitor and evaluate the stability of the preparation. Hearts which could not achieve stability for 15 minutes at this level of performance were discarded (approximately 3% of the preparations). Heart rate was held constant at 180/min with the right ventricular pacing wire 32. The "arterial" perfusate $pO_2$ was $600\pm5$ mm Hg. In one passage through the heart only 63% of the perfusate oxygen was extracted and $11\pm2\%$ of the perfusate lactate content was utilized indicating that oxygen delivery was adequate and that the myocardium was in an aerobic metabolic state during the control period.

Half-way through the 30 min. pre-ischemic control period the intraventricular balloon volume was adjusted to produce a developed, systolic pressure of approximately 80 mm Hg, with a diastolic pressure below 10 mm Hg. This balloon volume defined the "control ventricular volume" and was measured to $\pm0.05$ cc with a calibrated syringe; the control ventricular volume in 20 hearts was $0.59\pm0.03$ ml. The pre-ischemic developed pressure with the control ventricular volume in the balloon in the stretch group was $78.5\pm2.2$ mm Hg; in the no-stretch group it was $78.4\pm2.4$ mm Hg.

Coronary arterial flow was then turned off for 90 minutes. To simulate conditions which would be present during the ischemic arrest of cardiac surgery, the pacemaker was turned off and the intraventricular balloon was collapsed in both groups. Thus the heart went into an ischemic arrest.

In the no-stretch group of ten hearts the left ventricular volume was transiently filled to the control, pre-ischemic volume at 30, 60, and 90 min. of ischemia to measure the contracture pressure and any mechanical activity of the ventricle. At all other times the balloon was deflated to match the usual surgical condition.

In the stretch group of ten hearts the left ventricular balloon was expanded once every five minutes during the period of ischemic arrest by a hand-held syringe 14 for one second. The volume to be injected into the balloon was defined after 5 min. of ischemia as the volume required to increase the intraventricular pressure in the arrested ventricle to the pre-ischemia, control peak systolic pressure; this volume was called the "stretch volume". This volume was defined early in the arrested period before any significant myocardial contracture of stiffness had developed. Preliminary experiments indicated that this volume would produce enough stretch to rupture any contracture bonds without overstretching the myocardium to the point of decreasing recovery of contractile function. The average control preischemic balloon volume in the stretch group was $0.5\pm0.1$ ml; the average "stretch volume" was $1.2\pm0.1$ ml. The mean stretch volume of 1.2 ml was 2.4 times greater than the mean control diastolic volume of 0.5 ml. Since circumference varies as the cube root of the volume, injection of our stretch volume increased circumferential fiber stretch by approximately 34% above the control diastolic length.

Throughout the period of ischemic arrest, each heart of the stretch group was periodically stretched to the stretch volume. Specifically, every five minutes, the heart was stretched for a one second interval. The effect on contracture with each such stretching of the ventricular muscle is exemplified by the graph of FIG. 2 for a heart after 60 minutes of ischemia. Through the five minute interval of no stretch prior to this stretching action, the diastolic contracture of the heart muscle resulted in an increase in pressure to 20mm Hg with a 0.9ml control volume. Stretching of the muscle was attained by increasing the volume of the balloon to the stretch volume of 2.1 ml. Through the one second stretch period, the graph indicates an increase in the ventricular pressure to 90 mm Hg. The balloon was then returned to the control volume of 0.9 ml and the muscle relaxed completely to a point of negligible contracture. It can be seen then that this single filling and emptying of the ventricular balloon reversed the contracture which had occurred through the prior five minute interval.

At times during the 90 min. period of ischemia subsequent to the initial stretch in which the stretch volume was defined, as contracture and myocardial stiffness increased, injection of this stretch volume increased the intraventricular pressure in excess of the preischemic control peak systolic pressure. This can be seen in FIG. 3 in which the mean peak stretch pressure is plotted for each stretch interval. However, since the stretch volume was held constant during the ischemic arrest period, it is believed that a constant stretch was being applied to the fibers with each balloon filling despite the progressive increase in ventricular stiffness suggested by FIG. 3.

The peak ventricular pressure at the "stretch volume" ("peak stretch pressure") was an indirect measure of passive ventricular compliance. At 5 min. of ischemia the peak stretch pressure was $83\pm2$ mm Hg; this parameter decreased by 15 mm Hg over the subsequent 20 min. (FIG. 3) indicating an increase in passive ventricular compliance and possible stress relaxation or hysteresis resulting from the intermittent stretch. After 30 min. of ischemia, the peak stretch pressure progressively increased indicating an increase in effective stiffness of the ventricle. After 50 min. of ischemia peak stretch pressure was significantly greater than the 5 min. value, and by the end of the ischemic period it was $183\pm6$ mm Hg indicating a substantial resistance to ventricular filling to the level of the "stretch volume".

Figure 2:
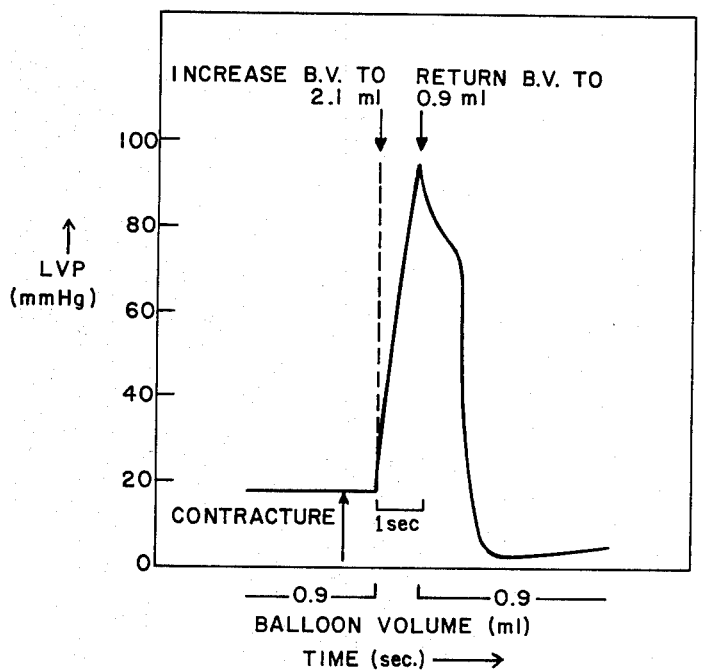
FIG. 2 is a graphical illustration of the fluid pressure within the ventricle-stretching balloon immediately before, during, and immediately after a stretching interval.

At 30, 60 and 90 min, of ischemia, immediately following a stretch, the intraventricular balloon volume was adjusted to the pre-ischemic, control value and any contracture or mechanical activity was recorded such as is shown in FIG. 2. After 90 min. of ischemia, reperfusion of both groups of hearts at the control coronary flow rate of 30 ml/min was begun with the intraventricular balloon filled to the control volume and paced at a rate of 180/min. The intraventricular balloon remained at the control volume throughout the reperfusion period in both groups.

The measured developed pressure, the derived rate of change of developed pressure and the measured diastolic contracture pressure, through the ischemic and reperfusion periods, resulting from the above experiment are indicated in FIG. 4. All date are reported as the mean ±SEM. Statistical analysis was done by means of the Student t-test. Asterisks indicate level of statistical significance for stretch vs. no stretch group at each time.

During the control, pre-ischemic period and at the initiation of ischemic arrest, the two groups had virtually identical levels of contractile function (FIG. 4A) and diastolic pressure (FIG. 4C). During ischemia contractile function was nil and the hearts in both groups were mechanically and electrically asystolic. In each group the left ventricular balloon was filled to the control pre-ischemia ventricular volume at 30, 60 and 90 min. to measure the contracture pressure (FIG. 4C). The no stretch group developed severe contracture during the ischemia period to a level of $110\pm14$ mm Hg intraventricular pressure after 90 min of ischemia. For the stretch group, the pre-stretch diastolic contracture pressure, measured at the control diastolic volume immediately prior to the stretch, at 30, 60 and 90 min. of ischemia was $1.9\pm0.6$, $12.7\pm2.7$ and $10.5\pm2.2$ mm Hg respectively. The 30 min. value was not significantly different from the pre-ischemic value of $3.5\pm0.8$. The values at 60 and 90 min. were significantly greater than the pre-ischemic and 30 min. values ($P<0.01$), but there was no significant difference between the 60 and 90 min. values.

FIG. 4C shows the degree of contracture in the stretch group, measured immediately after the "stretch volume" was injected and removed at 30, 60 and 90 min. of ischemia. Contracture pressure was measured with the control volume in the balloon; no contracture was present at these times during ischemia in the stretch group.

At the start of reperfusion in the no stretch group, diastolic contracture immediately intensified and then subsequently decreased. In the stretch group contracture developed with the start of reperfusion, reached its maximum early in the reperfusion period, and subsequently decreased roughly in parallel with the no stretch group. The stretch group had significantly less contracture pressure throughout the reperfusion period (FIG. 4C).

In the reflow period, the stretch group showed a trend toward a greater level of developed contractility (FIG. 4A). After 60 min. of reflow developed pressure in the no stretch group was $27\pm5\%$ of the control value compared to a $38\pm3\%$ recovery of developed pressure in the stretch group ($P=0.05-0.10$). Recovery of dP/dt (FIG. 4B) was $35\pm7\%$ in the no stretch group compared to $54\pm1\%$ in the stretch group ($P=0.05-0.10$). In the last 30 min. of the reflow period the stretch group was continuing to recover at a greater rate than the no stretch group. The rate of recovery of developed pressure was $6.7\pm1.0$ vs. $2.8\pm1.1$ mm Hg/30 min. ($P<0.025$) for the stretch vs. no stretch groups and the respective rates of recovery of dP/dt were $102\pm35$ vs. $61\pm19$ mm Hg/sec/30 min. ($P<0.05$). Thus, if the reflow period had been longer, it is possible that the stretch group would have recovered to a significantly higher level of contractile function.

Figure 3:
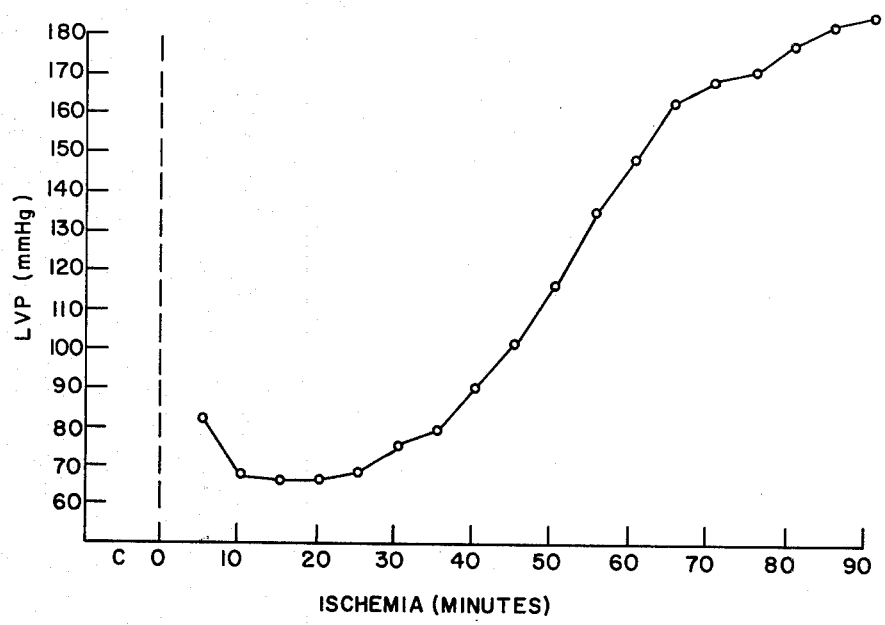
FIG. 3 is a graphical illustration of the peak stretch pressure for each stretch during the arrest period.

Our results demonstrated that a periodic (q 5 min.) stretch of the ventricular wall completely reversed the ischemic contracture which occurred. The intermittent stretching may have affected diastolic compliance during the ischemic period partly by a mechanism of stress relaxation or hysteresis. Stress relaxation or hysteresis was probably responsible for the decrease in the peak stretch pressure which was observed following the initial stretch at 5 min. of ischemia until 30 min. of ischemia. After 30 min. of ischemia, significant contracture occurred and the peak stretch pressure increased (FIG. 3). However, the maximum stress relaxation or hysteresis effect, i.e. the decrease in peak stretch pressure at 10–20 min. of ischemia was 15 mm Hg, and this 15 mm Hg decrease in ventricular pressure occurred at a balloon volume 2.4 times greater than the control diastolic volume. Since contracture pressure was measured at the control diastolic volume any effect of stress relaxation or hysteresis to decrease the contracture pressure would be substantially less than the 15 mm Hg effect measured at peak stretch volume. Since intermittent stretching decreased the contracture pressure by 110 mm Hg, measured at the control diastolic volume, a mechanism other than stress relaxation or hysteresis must be invoked. Furthermore, at the end of the five minute interstretch intervals the diastolic pressure in the stretch group remained quite low ($<13$ mm Hg). If the stretch had simply caused stress relaxation or hysteresis of the myocardium in contracture, the diastolic pressure should have increased to the level of the no stretch group by 5 min. after the stretch. The observation that the diastolic pressure remained relatively low in between stretches suggests that the intermittent stretching caused a relatively permanent change in the diastolic characteristics of the myocardium such as would result from the rupture of contracture or rigor bonds.

Ischemic contracture results from rigor bond formation between actin and myosin fibers; these rigor complexes form when the adenosine triphosphate concentration decreases below a critical level. Once contracture occurs, the rate of adenosine triphosphate breakdown is accelerated. At the end of the reperfusion period the creatine phosphate and adenosine triphosphate levels were significantly less than the control pre-ischemic level, but were not affect by the intermittent stretch. We did not measure tissue adenosine triphosphate and creatine phosphate at the end of the ischemic period, prior to reperfusion. If the intermittent stretch preserved tissue high energy phosphate levels during ischemia, this difference did not persist into the recovery period. The applied stretch probably ruptured the rigor complexes after they had formed and may not have prevented the accelerated adenosine triphosphate hydrolysis associated with rigor bond formation. This speculation is consistent with the lack of effect of the stretch on the high energy phosphate levels and also with the observation that a mild degree of contracture occurred during the 5 min. interstretch intervals. The intermittent stretch did not effect lactate metabolism or myocardial edema; therefore the effect of stretch on diastolic compliance was not mediated by alteration of one of these metabolic parameters.

The lack of metabolic effect of the intermittent stretch, the observation that the diastolic pressure remained low during the 5 min. interstretch intervals, and the complete absence of contracture when measured after a stretch, all strongly suggest that the intermittent stretching ruptured any rigor or contracture bonds which formed during the interstretch intervals.

The protective effect of the intermittent stretch on diastolic compliance persisted throughout the reperfusion period; however, the development of contracture during reperfusion was not completely prevented. This latter observation is not altogether surprising since contracture appears to be caused by different mechanisms during ischemia and during post-ischemia reperfusion. The increase in diastolic pressure at the time of reperfusion could also be due in part to an "erectile effect" where the increase in coronary perfusion pressure decreases myocardial compliance. Since no stretch was applied during the reperfusion period, the greater diastolic compliance in the stretch group during reperfusion was a persistent effect of the stretches which had been applied during the ischemic period. Perhaps the prolonged period of severe contracture in the no stretch group during ischemia directly damaged the contractile apparatus so that more severe contracture persisted during reperfusion; since the stretch group was prevented from developing severe contracture, the contractile apparatus may have been spared this damage. This speculation is also consistent with the observed trend toward a greater recovery of contractile function in the stretch group.

In this study, neither the frequency nor the amount of applied ventricular stretch were varied. A 5 min. interstretch interval was chosen because it was felt that this interval might be tolerated by the surgeon should it prove beneficial. It is possible that more frequent stretching would be more beneficial, that the same protective effect could be achieved with less frequent stretching or with a continuous stretch, or that applied stretch during the reperfusion period could lyse the contracture which occured at that time.

While the invention has been particularly shown and described with reference to a preferred embodiment thereof, it will be understood by those skilled in the art that various changes in form and detail may be made therein without departing from the spirit and scope of the invention as defined by the appended claims.

I claim:

1. A method of treating a heart during a period of arrest to protect the heart from the deleterious effects of sustained inactivity, the method comprising applying expanding force to the heart and expanding the ventricular volume a significant amount during the period of arrest to a volume greater than the arrested ventricular volume, the expansion causing stretching of the heart muscles.

2. A method of treating a heart during a surgical operation in which the heart is subjected to a period of arrest and the ventricle is and remains substantially evacuated of blood, the method comprising stretching the heart muscles during the period of arrest to reduce contracture of those muscles during the period of arrest.

3. A method as claimed in claim 1 or 2 wherein the heart muscles are stretched periodically during the period of arrest.

4. A method as claimed in claim 3 wherein the heart muscle is stretched about once every five minutes.

5. A method as claimed in claim 1 or 2 wherein the heart is stretched by a balloon positioned within the ventricle.

6. A method as claimed in claim 5 wherein the balloon is expanded periodically during the period of arrest.

7. A method as claimed in claim 6 wherein the balloon is expanded about once every five minutes.

8. A method as claimed in claim 5 wherein the balloon is expanded to a volume substantially greater than the diastolic volume of the ventricle.

9. A method as claimed in claim 8 wherein the balloon is expanded to a volume such that the pressure on the ventricle walls near the start of the period of arrest is about equal to the peak systolic pressure prior to arrest.

10. A method as claimed in claim 5 including monitoring the fluid pressure within the balloon when the balloon is expanded to a contracture monitoring volume and stretching the heart muscle by further expanding the balloon to a heart stretching volume greater than the contracture monitoring volume.

11. A method as claimed in claim 10 wherein the balloon is expanded to the heart stretching volume when the pressure at the contracture monitoring volume exceeds some predetermined threshold.

12. A method as claimed in claim 1 or 2 wherein the heart muscles are stretched by expanding the ventricular volume to a volume substantially greater than the diastolic ventricular volume.

13. A method as claimed in claim 12 wherein the heart muscle is stretched by expanding the ventricular volume such that the pressure on the ventricular walls near the start of the period of arrest is about equal to the peak systolic pressure prior to arrest.

14. A method as claimed in claim 1 or 2 wherein the heart muscle is stretched by filling the ventricle with a substantially incompressible fluid.

15. A method of treating a heart during a surgical operation in which the heart is subjected to a period of arrest and the ventricle is and remains substantially evacuated of blood, the method comprising periodically varying lengths of the heart muscle fibers during the period of arrest.

16. A method of protecting a heart from the deleterious effects of ischemic arrest, the method comprising applying an outward expansion force to the heart from within the heart ventricle and expanding the ventricular volume during the period of arrest to stretch the heart muscles and substantially reduce contracture of those muscles during the period of arrest.

17. A method of treating a heart during a surgical operation in which the heart is subjected to arrest for a period of arrest, the method comprising:
  positioning a balloon within a ventricle, there being a pressure transducer associated with the balloon to measure the fluid pressure therein and means for expanding the balloon to a monitoring volume with the balloon pressing against the ventricular muscle to monitor diastolic properties of the heart and to a larger stretching volume; and
  during the operation, expanding the balloon to the stretching volume to substantially reduce the contracture of the ventricular muscle throughout the period of arrest.

18. A method of treating a heart during a period of arrest to protect the heart from the deleterious effects of sustained inactivity, the method comprising expanding the ventricular volume a significant amount during the period of arrest to a volume substantially greater than the diastolic ventricular volume to stretch the heart muscles.

19. A method of treating a heart during a surgical operation in which the heart is subjected to a period of arrest, the method comprising stretching the heart muscles during the period of arrest by expanding the ventricular volume to a volume substantially greater than the diastolic ventricular volume to reduce contracture of the heart muscles during the period of arrest.

20. A method as claimed in claim 18 or 19 wherein the heart is stretched by a balloon positioned within the ventricle.

21. A method as claimed in claim 20 wherein the balloon is expanded to a volume such that the pressure on the ventricle wall near the start of the period of arrest is about equal to the peak systolic pressure prior to arrest.

22. A method as claimed in claim 18 or 19 wherein the heart muscle is stretched by expanding the ventricular volume such that the pressure on the ventricular walls near the start of the period of arrest is about equal to the peak systolic pressure prior to arrest.

23. A method of treating a heart during a period of arrest to protect the heart from the deleterious effects of sustained inactivity, the method comprising positioning a balloon within the ventricle, monitoring the fluid pressure within the balloon when the balloon is expanded to a contracture monitoring volume, and stretching the heart muscle by further expanding the balloon to a heart stretching volume greater than the contracture monitoring volume to thus expand the ventricular volume a significant amount during the period of arrest.

24. A method of treating a heart during a surgical operation in which the heart is subjected to a period of arrest, the method comprising positioning a balloon within the ventricle, monitoring the fluid pressure within the balloon when the balloon is expanded to a contracture monitoring volume, and stretching the heart muscle by further expanding the balloon to a heart stretching volume greater than the contracture monitoring volume to reduce contracture of the heart muscles during the period of arrest.

25. A method as claimed in claim 23 or 24 wherein the balloon is expanded to the heart stretching volume when the pressure at the contracture monitoring volume exceeds some predetermined threshhold.

* * * * *